United States Patent
van den Ende et al.

(10) Patent No.: US 10,575,780 B2
(45) Date of Patent: Mar. 3, 2020

(54) MEASURING OF A PHYSIOLOGICAL PARAMETER USING A WEARABLE SENSOR

(71) Applicant: KONINKLIJKE PHILIPS N.V., Eindhoven (NL)

(72) Inventors: Daan Anton van den Ende, Breda (NL); Reinder Haakma, Eindhoven (NL); Mark Thomas Johnson, Eindhoven (NL); Frederick Maria Boekhorst, Valkenswaard (NL); Milica Kovacevic Milivojevic, Eindhoven (NL); Franciscus Johannes Gerardus Hakkens, Eersel (NL); Achim Hilgers, Alsdorf (DE); Cornelis Petrus Hendriks, Eindhoven (NL); Rene Leonardus Jacobus Marie Ubachs, Eindhoven (NL); Eduard Gerard Marie Pelssers, Panningen (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 15/536,283

(22) PCT Filed: Dec. 1, 2015

(86) PCT No.: PCT/EP2015/078114
§ 371 (c)(1),
(2) Date: Jun. 15, 2017

(87) PCT Pub. No.: WO2016/096391
PCT Pub. Date: Jun. 23, 2016

(65) Prior Publication Data
US 2017/0347957 A1    Dec. 7, 2017

(30) Foreign Application Priority Data

Dec. 18, 2014 (EP) .................................. 14198836

(51) Int. Cl.
*A61B 5/00* (2006.01)
*A61B 8/00* (2006.01)
(Continued)

(52) U.S. Cl.
CPC ........ *A61B 5/6843* (2013.01); *A61B 5/02427* (2013.01); *A61B 5/02438* (2013.01);
(Continued)

(58) Field of Classification Search
CPC ... A61B 5/6843; A61B 5/6844; A61B 5/6885; A61B 5/6886; A61B 5/2438; A61B 5/0245; G06F 3/016
See application file for complete search history.

(56) References Cited

U.S. PATENT DOCUMENTS 4,987,900 A * 1/1991 Eckerle .............. A61B 5/02241
                                                        600/485
5,261,412 A * 11/1993 Butterfield ......... A61B 5/02255
                                                        600/485
(Continued)

FOREIGN PATENT DOCUMENTS

EP    3015948 A2 *   5/2016 ............... A44C 5/04
JP    06178764 A     6/1994
(Continued)

*Primary Examiner* — Michael W Kahelin
*Assistant Examiner* — Sana Sahand

(57) ABSTRACT

An apparatus comprises a sensor for measuring a physiological parameter of a subject, wherein the physiological parameter sensor is adapted to be worn by the subject; an actuator comprising an electro-active polymer material, EAP, portion for adjusting the position of the physiological parameter sensor relative to the subject; a feedback sensor for measuring movement of the physiological parameter sensor and/or the subject; a controller configured to process (Continued)

the measurements of the feedback sensor and to adjust the position of the actuator based on information from the feedback sensor.

20 Claims, 7 Drawing Sheets

(51) Int. Cl.
*F03G 7/00* (2006.01)
*A61B 5/024* (2006.01)
*A61B 5/0402* (2006.01)
*H01L 41/09* (2006.01)
*H01L 41/193* (2006.01)
*A61B 5/0408* (2006.01)
*A61B 5/1455* (2006.01)

(52) U.S. Cl.
CPC .......... *A61B 5/0402* (2013.01); *A61B 5/6824* (2013.01); *A61B 5/6844* (2013.01); *A61B 5/7207* (2013.01); *A61B 8/44* (2013.01); *F03G 7/005* (2013.01); *H01L 41/09* (2013.01); *H01L 41/193* (2013.01); *A61B 5/02416* (2013.01); *A61B 5/0408* (2013.01); *A61B 5/14551* (2013.01)

(56) References Cited

U.S. PATENT DOCUMENTS

| | | | |
|---|---|---|---|
| 6,491,647 B1* | 12/2002 | Bridger | A61B 5/021 128/900 |
| 6,876,135 B2* | 4/2005 | Pelrine | A43B 3/0005 310/317 |
| 7,339,572 B2 | 3/2008 | Schena | |
| 7,641,614 B2* | 1/2010 | Asada | A61B 5/02225 600/485 |
| 8,471,438 B2 | 6/2013 | Yamamoto et al. | |
| 2002/0013534 A1 | 1/2002 | Muramatsu et al. | |
| 2007/0265140 A1 | 11/2007 | Kim et al. | |
| 2007/0287923 A1* | 12/2007 | Adkins | A61B 5/412 600/485 |
| 2008/0033275 A1 | 2/2008 | Blank et al. | |
| 2008/0194917 A1 | 8/2008 | Muehlsteff et al. | |
| 2011/0247321 A1* | 10/2011 | Streeter | A61F 2/68 60/327 |
| 2014/0018648 A1 | 1/2014 | Pao et al. | |
| 2014/0276134 A1* | 9/2014 | Lin | A61B 5/6843 600/485 |
| 2014/0277739 A1 | 9/2014 | Kornbluh et al. | |
| 2014/0288390 A1* | 9/2014 | Hong | A61B 5/02427 600/301 |
| 2014/0296658 A1* | 10/2014 | Yuen | A61B 5/6885 600/301 |
| 2014/0364749 A1* | 12/2014 | Varma | A61B 5/22 600/494 |
| 2015/0207914 A1* | 7/2015 | Hunt | H04M 19/047 340/407.1 |
| 2017/0319136 A1* | 11/2017 | Kosonen | G06F 1/163 |

FOREIGN PATENT DOCUMENTS

| | | |
|---|---|---|
| JP | 2002165766 A | 6/2002 |
| JP | 2006102191 A | 4/2006 |
| JP | 2007319343 A | 12/2007 |
| WO | 2009006318 A1 | 1/2009 |
| WO | 2013038285 A1 | 3/2013 |

\* cited by examiner

MEASURING OF A PHYSIOLOGICAL PARAMETER USING A WEARABLE SENSOR

CROSS-REFERENCE TO PRIOR APPLICATIONS

This application is the U.S. National Phase application under 35 U.S.C. § 371 of International Application No. PCT/EP2015/078114, filed on Dec. 1, 2015, which claims the benefit of European Application No. 14198836.0, filed Dec. 18, 2014. These applications are hereby incorporated by reference herein, for all purposes.

FIELD OF THE INVENTION

This invention relates to sensors for measuring a physiological parameter of a subject, wherein the sensor can be worn by a user. For example a wearable photoplethysmographic (PPG) sensor, a wearable electrocardiogram sensor, a wearable ultrasound sensor, a wearable heart rate sensor, or a wearable skin monitoring sensor. In particular, the invention relates to an apparatus comprising a wearable sensor for maintaining contact or maintaining a particular distance of separation between the wearable sensor and the user.

BACKGROUND OF THE INVENTION

It is becoming increasingly popular to monitor a physiological parameter of a subject using an apparatus including a wearable device. Such devices are convenient to use as they offer increased freedom of movement for the user whilst a physiological parameter is being monitored. In this way, it is possible to measure physiological parameters in a variety of circumstances, for example at different levels of physical exertion of the subject.

The physiological parameter sensor may be mounted to the user differently in different applications. The position of the mounted physiological parameter sensor relative to the subject when the sensor may vary according to the parameter to be measured, the type of physiological parameter sensor, and/or the circumstances in which physiological sensing takes place. In some cases, the physiological parameter sensor should be in contact with the user's body. In other cases, the physiological parameter sensor should be separated from the subject's body. An important problem with respect to wearable sensors is ensuring that the contact pressure or separation between the physiological parameter sensor and the user's body is maintained at a constant level since the signal obtained during physiological sensing is affected by the relative position of the wearable sensor and the user. For instance, in PPG monitoring, a steady distance between the light sensor and the skin is desired for optimal stability of the sensor signal. For ultrasound transducer patches, good contact with the skin is imperative for high quality images. Similarly, the electrodes of ECG monitoring devices are sensitive to contact pressure.

Therefore, one problem that can occur during monitoring of a physiological parameter using an apparatus including a wearable sensor is that the position of the sensor relative to the body of the user may change as a consequence of movement of the user, resulting in a change in the measured data. Movement of the user resulting in a change in the relative position of the wearable sensor and the user causes motion artefacts to be present in the measured data. While motion artefacts can be filtered out digitally, this approach can negatively impact the quality of the measurement data obtained using the wearable sensor.

There is therefore a need for a wearable device for measuring a physiological parameter that can be operated to obtain high quality data.

SUMMARY OF THE INVENTION

The need as at least partly addressed with the current invention as defined by the independent claims. The dependent claims provide advantageous embodiments.

According to examples in accordance with an aspect of the invention, there is provided a wearable physiological sensor apparatus, comprising:

a sensor for measuring a physiological parameter of a subject, wherein the sensor is adapted to be worn by the subject;

an actuator comprising an electro-active polymer material portion for adjusting the position of the sensor relative to the subject;

a feedback sensor for measuring movement of the physiological parameter sensor and/or the subject; and a controller configured to process a measurement of the feedback sensor and to control the actuator to adjust the position of the sensor based on the measurement of the feedback sensor.

The apparatus comprises a wearable device including a sensor (this may be a physiological parameter sensor) for measuring a physiological parameter of a subject by contacting it with, or even attaching the wearable device to, the subject. A subject or user can be a human being or animal. A feedback sensor is provided to measure a parameter, wherein the value of the parameter or change in the value of the parameter indicates that the relative position of the physiological parameter sensor and the subject (user) has changed. The feedback sensor may measure whether there is contact between the physiological parameter sensor and the subject and/or the contact pressure between the physiological parameter sensor and the subject, and/or the distance between the physiological parameter sensor and the subject. Note that the feedback sensor may be implemented by the sensor for measuring the physiological parameter itself. The measurements of the feedback sensor are sent to the controller which can receive and determine whether the position of the sensor has changed with respect to the user based on one or more measurements of the feedback sensor.

If a change in the relative position of the sensor for measuring the physiological parameter and the subject (user) is detected, the controller sends an actuation signal to the actuator, causing the actuator to move to an actuated configuration. This is a configuration wherein the shape or configuration of the actuator changes. The actuator and physiological parameter sensor are arranged such that the actuated configuration causes a change of the position of the sensor for measuring the physiological parameter relative to the subject.

By using an electroactive polymer actuator, the device can operate with low power consumption and therefore enable monitoring over a prolonged period of time with a small power supply. It also enables the actuator to be small and light so that it gives minimum discomfort to the user. Preferably of this purpose the device uses an electroactive polymer as actuation material within the actuator.

The feedback sensor may be configured to measure a change in the contact force between the physiological parameter sensor and the subject. In use, the feedback sensor may be positioned between the physiological parameter sensor and the user's body. The actuator may be arranged to adjust the contact pressure between the sensor and the subject, and the controller may adjust the contact of the physiological parameter sensor with the subject using the actuator, according to the measured movement.

The apparatus may further comprise a coupling member disposed on the physiological parameter sensor. The coupling member may be arranged between the physiological parameter sensor and the subject in use. In this way, the parameter sensor can be positioned at a desired distance from the user's body, as the coupling member serves as a spacer to separate the physiological parameter sensor from the user's body. The physiological parameter sensor can then be maintained at a particular distance from the user's body during use.

The feedback sensor may be configured to measure a change in a distance between the physiological parameter sensor and the subject i.e. the distance separating the physiological parameter sensor and the subject. For example, the separation distance may be the distance between the subject's body and a reference point on the physiological parameter sensor. In another example, the separation distance may be the shortest distance between the subject's body and the physiological parameter sensor. Alternatively, the feedback sensor may be configured to measure displacement (change in separation distance) of the parameter sensor relative to the subject.

The physiological parameter sensor may comprise: a housing having walls which define an internal area; and a sensor element disposed inside the internal area of the housing, wherein the feedback sensor is configured to measure movement of the housing relative to the subject. A change in the position of the housing may cause the parameter measured by the sensor element to change, indicating that the physiological parameter sensor has moved relative to the user.

The physiological parameter sensor may comprise the feedback sensor, and the controller may be configured to process a signal from the physiological parameter sensor and to adjust the position of the actuator based on the signal of the physiological parameter sensor. The physiological parameter sensor may comprise a sensor element that is for measuring a physiological parameter and for measuring movement of the physiological parameter sensor and/or the subject.

The physiological parameter sensor may comprise: a housing having walls which define an internal area; a light source disposed in the internal area of the housing; and a light sensor disposed inside the internal area of the housing, and wherein the controller is configured to process a signal of the light sensor and to adjust the position of the actuator based on the signal of the light sensor.

The apparatus may further comprise an external light sensor disposed outside of the housing, and wherein the controller is configured to process a signal of the external light sensor and to adjust the position of the actuator based the light signal of the external light sensor and the light sensor of the physiological parameter sensor. The controller may be configured to adjust the position the actuator based on a difference of the light signal of the external sensor and the light signal of the light sensor of the physiological parameter sensor.

For example, the external light sensor may measure ambient lighting conditions and the controller may be configured to compare a change in the light signal of the light sensor of the physiological parameter sensor to the light signal of the external light sensor. In this way, the controller may distinguish light intensity changes as a result of the broken skin contact from those resulting from other causes.

The apparatus may further comprise:
a signal generator adapted to:
generate a first electrical AC signal, for use in sensing, having a first frequency;
generate a second electrical AC signal, for use in actuation, having a second frequency wherein the second frequency is substantially the same as the first frequency;
apply the first electrical signal to the physiological parameter sensor; and
apply the second electrical signal to the actuator; and
a detector for detecting a variation in the first electrical signal with respect to the second electrical signal.

Movement of the physiological parameter sensor may affect the amplitude of the first signal. For example, if the physiological parameter sensor loses contact with the user this may cause amplitude variations to be present in the first signal. By comparing variations in the first signal, in particular those that occur at the frequency of the second signal using the detector, it is possible to monitor the difference in the first signal and identify when movement of the physiological parameter sensor took place.

The actuator may further comprise a strain sensitive electrode portion disposed on the EAP portion; and the apparatus further comprises:
a first voltage source arranged to apply a first voltage to the EAP portion of the actuator; and
a second voltage source arranged to apply a second voltage to the strain sensitive electrode portion of the actuator;
wherein the controller is arranged to measure a change in resistivity of the strain sensitive electrode and to adjust the position of the actuator based on the measured change in resistivity.

The physiological parameter sensor may comprise a housing and the actuator is arranged to exert a force on the housing in response to an actuation signal from the controller. In use, the relative position of the physiological parameter sensor and a user can be adjusted by changing the shape of the actuator to move the housing and thereby move the physiological parameter sensor.

According to another aspect of the invention, there is provided a method for measuring a physiological parameter using the device defined above, comprising:
(i) obtaining a signal using the feedback sensor;
(ii) determining if the physiological parameter sensor has moved relative to the subject, based on the signal of the feedback sensor; and
(iii) if the physiological parameter sensor has moved relative to the subject, adjusting the position of the actuator.

The controller may determine that the physiological parameter sensor has moved if measurements of the feedback sensor show that a parameter corresponding to movement of the physiological parameter sensor (e.g. a parameter indicating contact, contact pressure or separation distance) has changed. By adjusting the position of the actuator, the position or configuration of the physiological parameter sensor may be adjusted. Alternatively, the contact pressure between the subject and the physiological parameter sensor may be adjusted. With this method, it is possible to measure a physiological parameter of a subject using a wearable device, and obtain high quality data even if the subject moves during the measurement process.

Step (ii) may comprise comparing a measurement of contact pressure to a reference value for contact pressure. In this way, the current contact pressure is compared to a desired contact pressure which is the contact pressure that is required or optimal for carrying out a measurement of a physiological parameter using the physiological parameter sensor. If the contact pressure is different to the reference contact pressure, this indicates that the physiological parameter sensor has moved, and that a compensation step may need to be performed.

Step (ii) may comprise comparing a measured separation distance to a reference separation distance. The separation distance of the physiological parameter sensor (for example the housing, or the sensor element) is compared to a desired separation distance which is the separation distance that is required or optimal for carrying out a measurement of a physiological parameter using the physiological parameter sensor. If the separation distance is different to the reference separation distance, this indicates that the physiological separation distance has changed, and that a compensation step may need to be performed (i.e. the actuator should be moved).

The actuator may be adjusted to directly contact the physiological parameter sensor. In this way, movement of the physiological parameter sensor relative to the subject is compensated for since the actuator exerts a force on the physiological parameter sensor causing the physiological parameter sensor to move back to the position it was in before it was disrupted by movement of the subject.

The method may further comprise the steps of:

(iv) applying a first AC signal having a first frequency to the actuator;

(v) applying a second AC signal having a second frequency to the physiological parameter sensor, wherein the second frequency is the same as the first frequency; and (vi) comparing the first AC signal and the second AC signal to determine if the physiological parameter sensor has moved.

Movement of the physiological parameter sensor will lead to a change in the second signal. Therefore, when the first signal is compared to the second signal it is possible to accurately calculate the point at which the physiological parameter sensor began to move. This information can then be used to calculate the magnitude of the actuation signal required to compensate for movement of the physiological parameter sensor.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
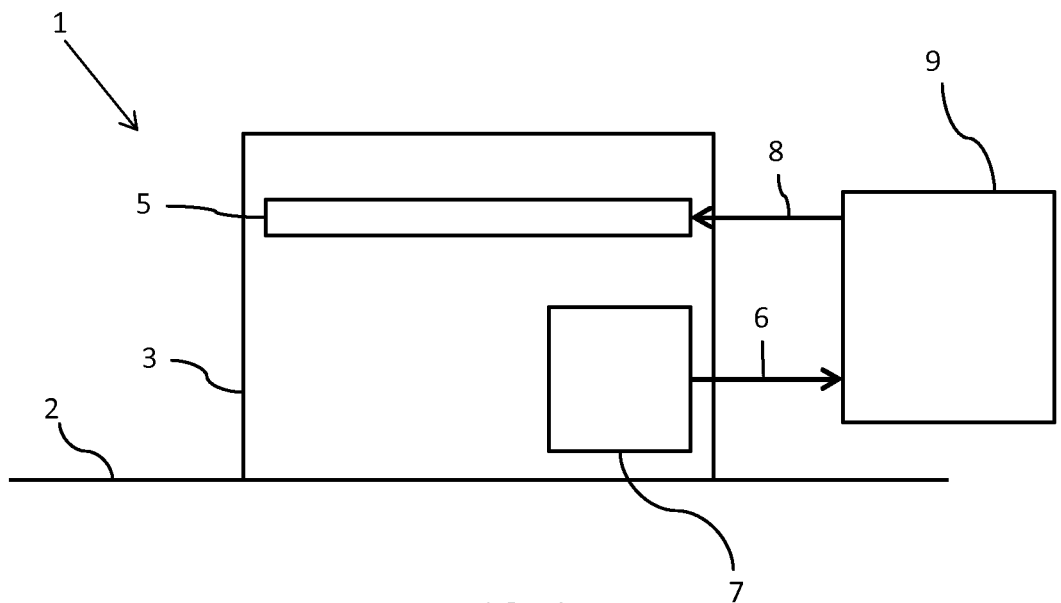
FIG. 1 is a block diagram of a wearable sensor apparatus.

FIG. 1 is a schematic block diagram illustrating an apparatus 1 according to an example of the invention. The invention provides an apparatus 1 including a physiological parameter sensor 3 adapted to be worn by a subject; an actuator 5, comprising an electroactive polymer material, for adjusting the position of the physiological parameter sensor 3 relative to the subject 2; a feedback sensor 7 for measuring movement of the physiological parameter sensor relative to the subject and a controller 9 configured to process measurements of the feedback sensor 7 and to adjust the position of the actuator 5 based on information from the feedback sensor 7.

The feedback sensor 7 is arranged to detect relative movement of the physiological parameter sensor 3 with respect to the user's body 2. For example, the feedback sensor 7 may be a contact sensor arranged to detect if the physiological parameter unit is in contact with the subject. For example, the feedback sensor may be an optical sensor or a sensor for measuring electrical resistance. Alternatively, the feedback sensor may be a pressure sensor, arranged to measure the contact pressure between the physiological parameter sensor 3 and the user's body, since a change in the contact pressure indicates that the relative position of the physiological parameter sensor and the body has changed. The feedback sensor may be capable of measuring the distance between the physiological parameter sensor 3 and the user's body or for measuring displacement of the physiological parameter sensor 3 relative to the subject.

The feedback sensor, for example, may be a capacitive sensor. This allows a user to calibrate the apparatus 1 so that the physiological parameter sensor 3 is at an optimal separation distance from a user's body during use. Once an initial separation distance is established, any change in the separation distance is measured by the feedback sensor 7, and the controller 9 controls the actuator 5 to compensate for the change. In this way, the physiological parameter sensor 3 is maintained at a desired separation distance during use, even if the user is moving, whilst the physiological parameter measurements are being taken.

The feedback sensor 7 sends a feedback signal 6 with information about contact, the contact pressure or the separation distance between the physiological parameter sensor 3 and the user's body to the controller 9, which processes the feedback signal 6 and determines whether the position of the physiological parameter sensor 3 has moved relative to the user's body. If a change in position is detected, the controller 9 sends an actuation signal 8 to the actuator 5 to adjust the position of the actuator 5. The controller 9 may calculate the signal required to compensate for the change in relative position of physiological parameter sensor 3 and the user's body, and to send this signal to the actuator 5. For example, the controller 9 may send a DC signal having an amplitude that corresponds to the change in shape of the actuator 5 that is required to compensate for the detected change in the relative position of the physiological parameter sensor 3 and the user's body. Alternatively, the controller 9 may send a signal that corresponds to a small change in the position of the actuator 5 repeatedly, until contact or the desired distance of separation is re-established.

The apparatus 1 may comprise a single unit or device for measuring a physiological parameter of the subject, the device being worn or carried by the subject. In alternative examples, the controller 9 (or the functions performed by the controller 9) can be located remotely from the physiological parameter sensor 3, feedback sensor 7 and actuator 5 (for example in a unit that is worn on a different part of the body of the subject, in a base unit or computer that can be located in the subject's home, or a remote server located in the premises of a healthcare service provider), in which case the apparatus 1 will comprise a sensor unit to be worn by the subject (that is similar to that shown in FIG. 1) and that comprises suitable transmitter, transceiver or communication circuitry for transmitting the measurements to a controller in the remote unit. In either example, the apparatus 1 can be part of a monitoring system which comprises a display or other visual indicator (that can themselves be part of or separate from the apparatus 1) that can be used to indicate the measured physiological parameter to the subject or a clinician.

The physiological parameter sensor 3 may be an optical sensor, an ultrasound sensor, an ECG sensor or any other type of sensor for measuring a physiological parameter. The specific arrangement of the apparatus 1, physiological parameter sensor 3 and actuator 5 depends on the nature of the physiological parameter sensor 3 and the actuator 5.

With this apparatus 1, it is possible to measure a physiological parameter of subject whilst the subject is moving, since interference due to movement of the subject is reduced by the feedback sensor/actuator arrangement. Movement of the physiological parameter sensor 3 is sensed by the feedback sensor 7, and compensated for using the actuator 5.

The actuator 5 comprises a portion of electroactive polymer material which converts an electrical drive signal to physical movement. The actuator which provides adequate displacement for stabilisation in this application whilst also having a small footprint.

Advantages of EAPs include low power, small form factor, flexibility, noiseless operation, accuracy, the possibility of high resolution, fast response times, cyclic actuation, and a large range of possible actuation frequencies, such as 0-1 MHz, most typically below 20 kHz.

Further, EAPs can easily be manufactured into various shapes. Thus, electro-active polymer materials can easily be integrated into wearable apparatus 1 (such as clothing, a watch or a patch). They require little power to operate which makes them particularly suited to portable applications, and their small size means that the overall blood flow in the limb or digit is not appreciably affected when pressure is applied to the physiological parameter sensor 3.

The use of an actuator comprising an EAP portion enables functions which offer a big advantage over conventional apparatus, due to the combination of a relatively large deformation and force in a small volume or thin form factor, compared to common actuators.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (volts per meter) but low currents. Polymer layers are usually thin to keep the driving voltage as low as possible. Ionic EAPs are activated by an electrically induced transport of ions and/or solvent. They usually require low voltages but high currents. They require a liquid/gel electrolyte medium (although some material systems can also operate using solid electrolytes).

Both classes of EAP have multiple family members, each having their own advantages and disadvantages.

A first notable subclass of field driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nafion® and Flemion®.

Another notable subclass of Ionic polymers is Conjugated/conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In some cases, thin film electrodes are added when the polymer itself lacks sufficient conductivity (dimension-wise). The electrolyte can be a liquid, a gel or a solid material (i.e. complex of high molecular weight polymers and metal salts). Most common conjugated polymers are polypyrolle (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

Figure 2A:
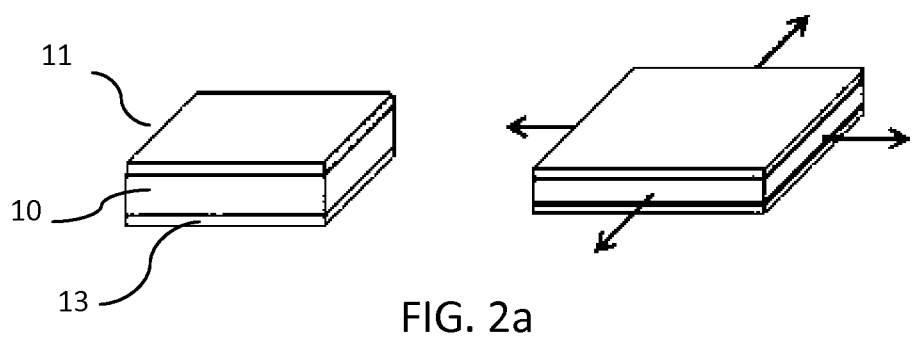
FIG. 2a shows an electroactive polymer layer between two flexible electrodes.
Figure 2B:
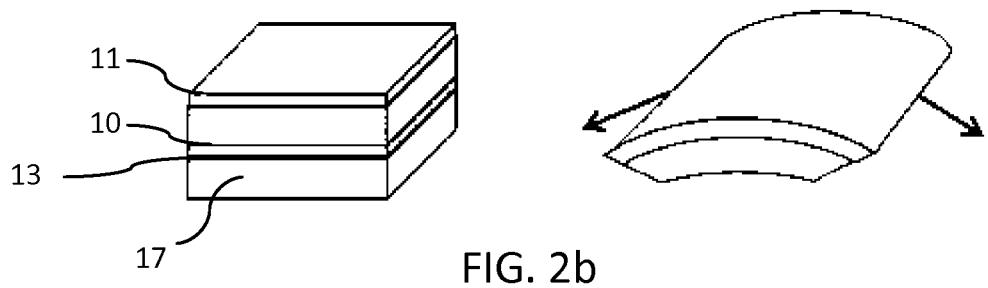
FIG. 2b shows the device of FIG. 2a disposed on a passive layer.

FIGS. 2a and 2b show two possible operating modes for an EAP device.

The device comprises an electroactive polymer layer 10 sandwiched between electrodes 11, 13 on opposite sides of the electroactive polymer layer 10.

FIG. 2a shows a device which is not clamped. A voltage is used to cause the electro-active polymer layer to expand in all direction.

FIG. 2b shows a device which is designed so that the expansion arises only in one direction. The device is supported by a carrier layer 17. A voltage is used to cause the electroactive polymer layer 10 to change shape, for example to curve or bow.

The nature of this movement for example arises from the interaction between the active layer 10 and the passive carrier layer 17. To obtain the asymmetric curving around an axis as shown, molecular orientation (film stretching) may for example be applied, forcing the movement in one direction.

The expansion in one direction may result from the asymmetry in the EAP, or it may result from asymmetry in the properties of the carrier layer, or a combination of both.

In general, and as shown in FIGS. 3, 4, 5, 9 and 10, the physiological parameter sensor comprises a housing 20 and a sensor element 12 inside the housing, wherein the sensor element 12 is for measuring a physiological parameter.

In some embodiments, and as shown in FIGS. 3, 4, 5, 9 and 10, the actuator 5 is arranged such that when a signal from the controller 9 causes the actuator 5 to bow, the actuator 5 presses down on a portion of the physiological parameter sensor 3 and pushes it towards the user's body. For example, FIGS. 3, 4, 9 and 10 show examples in which the actuator is arranged to exert a force on the sensor element 12 of the physiological parameter sensor 3. FIG. 5 shows another example, having a different type of arrangement, in which the actuator is configured to exert a force on the housing 20 of the physiological parameter sensor.

Figure 10A:
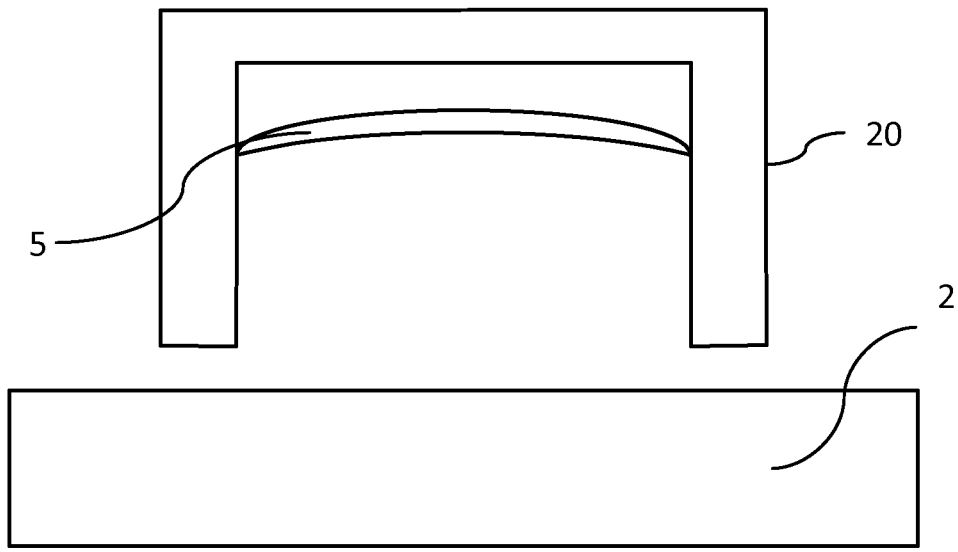
FIGS. 10a and 10b show a physiological parameter sensor and actuator according to another example.
Figure 10B:
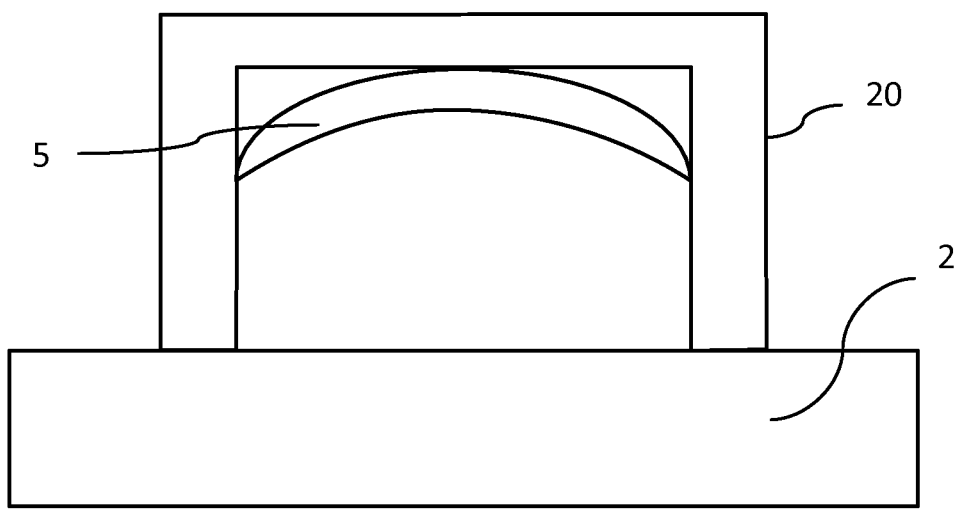

In alternative examples, the actuator 5 is arranged such that a change in position of the actuator 5 in response to a signal from the controller 9 causes a small vacuum to be formed inside a housing of the physiological parameter sensor 3, causing the contact pressure between the physiological parameter sensor 3 and the user's body to increase; this type of arrangement is shown in FIGS. 10a and 10b.

The various examples will now be described in greater detail.

Figure 3:
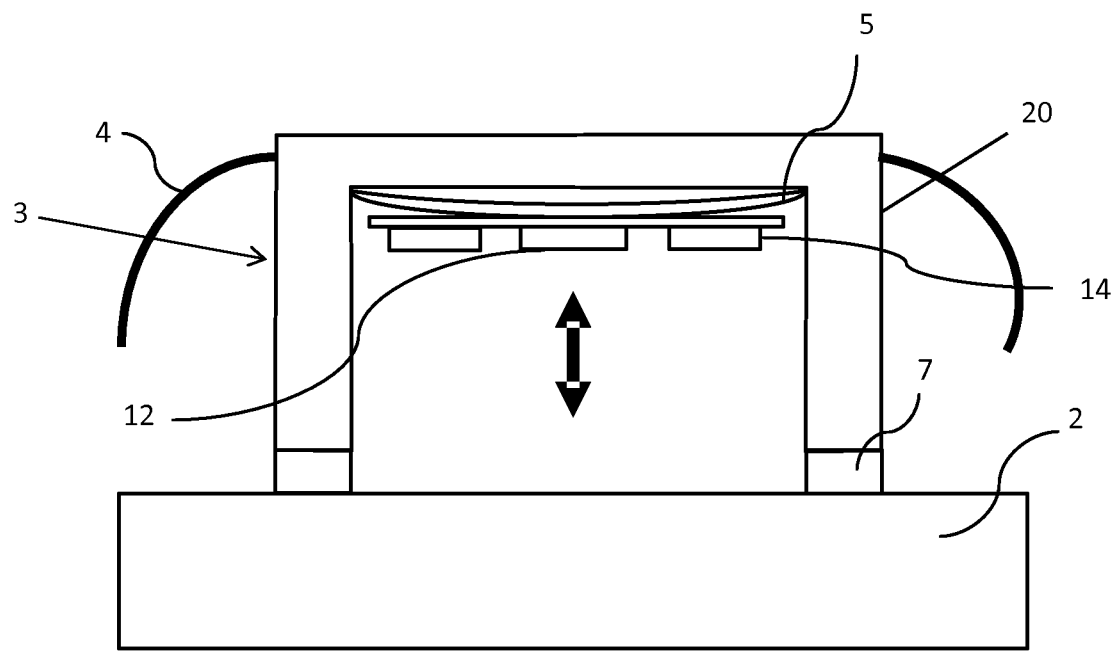
FIG. 3 shows a wearable device of an apparatus according to an example, in cross section.

FIG. 3 shows an example, in which the feedback sensor 7 measures the contact pressure between the physiological parameter sensor 3 and the subject or the distance of separation between the physiological parameter sensor 3 and the subject 2.

The physiological parameter sensor 3 can be for measuring the heart rate, or parameters related to the heart rate (such as heart rate variability, etc.), and/or blood oxygen saturation (SpO2). In the former case the physiological parameter sensor 3 can be a photoplethysmography (PPG) sensor, and in the former or latter case the physiological parameter sensor 3 can be an SpO2 sensor.

The physiological parameter sensor 3 is adapted to be attached to a body part of a user. For example, the physiological parameter sensor may be attached a user's arm, using a strap 4. The physiological parameter sensor 3 includes a housing 20 which is adapted to interface with a user's body, a light source 14 (e.g. an LED) and a sensor element 12 for measuring light.

In an exemplary, non-limiting, implementation, the light source 14 can be a green light emitting diode (LED) that emits light at wavelengths in the range of 500-600 nm (or a red LED that emits light at wavelengths in the range of 600-700 nm) and the photodetector or other type of light sensor 12 can be sensitive to light at wavelengths below 1000 nm. Also as appreciated by those skilled in the art, an SpO2 sensor comprises a plurality of light sources 14 and at least one light sensor 12 that is sensitive to at least the wavelengths of light emitted by the light sources 14. The plurality of light sources 14 can include, for example, a near-infrared LED that emits light at wavelengths in the range of 800-1000 nm and a red LED that emits light at wavelengths in the range of 600-700 nm. The light sensor 12 can be sensitive to light at wavelengths below 1000 nm (although alternatively separate light sensors 12 that are respectively sensitive to light in the ranges of 800-1000 nm and 600-700 nm can be provided).

In alternative examples, the physiological parameter sensor 3 could be an ECG sensor comprising an electrode arranged to contact the subject in use or an ultrasound sensor comprising a transducer disposed within a housing.

In alternative examples the physiological parameter sensor 3 can be another type of light-based sensor that is sensitive to the quality of the contact between the subject and the sensor element 12, such as, for example, based on laser Doppler, laser speckle velocimetry, near-infrared spectroscopy and microcirculation microscopy.

The apparatus includes an actuator 5 which is of electroactive polymer material and is arranged with respect to the physiological parameter sensor 3 in such a way that adjustment of the position of the actuator 5 results in a change in the distance between the sensor element 12 and the user's body, in use. The actuator 5 is arranged to exert a force on the sensor element 12 of the physiological parameter sensor 3, in response to a signal from the controller 9. In this example, the actuator 5 is positioned internally against a roof portion of the housing 20 that extends horizontally between opposite walls of the housing 20. In use, when the actuator 5 is moved to the actuated configuration, the light sensor 12 and light source 14 are pushed downward, away from the roof of the housing towards the subject.

In some examples the light sensor 12 and light source 14 can be located close to (e.g. next to) each other within the apparatus in which case the light sensor 12 can measure the light from the light source 14 that reflects from the part of the body of the subject that the physiological parameter sensor 3 is in contact with, or they can be arranged on generally opposite sides of the part of the body of the subject (in which case the light sensor 12 measures light from the light source 14 that is transmitted by (i.e. that passes through) the part of the body of the subject).

The light source 14 and sensor element 12 are disposed within a cavity defined by walls of the housing 20, and a feedback sensor 7 is attached to a bottom portion of the housing 20 opposite to the roof of the cavity. The feedback sensor 7 is a pressure sensor, for example a capacitive sensor, a piezoelectric sensor or a strain sensor. In use, the feedback sensor 7 measures the contact pressure between the housing 20 of the physiological parameter sensor 3 and the user's body. The controller 9 processes these measurements and determines whether the physiological parameter sensor 3 has moved relative to the user's body 2 (contact pressure has changed).

In another example, the feedback sensor 7 is configured to measure whether the physiological parameter sensor 3 is in contact with the user's body or not (if contact pressure is negligible). For example, the feedback sensor 7 is an optical sensor or a sensor for measuring electrical resistance. The controller 9 is configured to process measurements of the feedback sensor 7 and to determine whether the physiological parameter sensor 3 is in contact with the user's body. If it is determined that the physiological parameter sensor 3 is not in contact with the user's body, the controller 9 sends a signal to the actuator 5 causing the actuator 5 to adjust its position in order to move the physiological parameter sensor 3 towards the user's body and to re-establish contact.

In another example, the feedback sensor 7 is configured to measure the distance between the housing 20 and the subject 2 in use.

Figure 4:
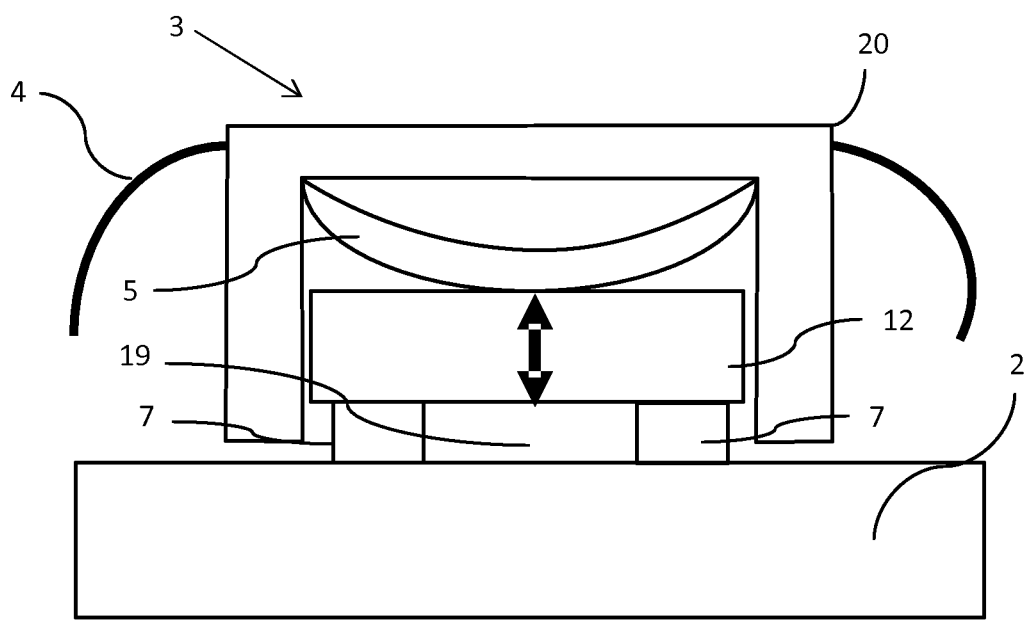
FIG. 4 shows a wearable device of an apparatus according to another example, in cross section.

FIG. 4 shows an example, in which the pressure of contact between the physiological parameter sensor 3 and the user's body 2 is controlled. In this example, the physiological parameter sensor 3 is an ultrasound sensor. The physiological parameter sensor 3 includes a housing 20 and a sensor element 12 disposed within the housing. The sensor element 12 is a sensor for measuring a physiological parameter, for example a transducer for making ultrasound measurements. The sensor element 12 is positioned in a cavity defined by the walls of the housing 20. The actuator 5 is arranged relative to the sensor element 12, such that when the actuator is actuated in response to a signal from the controller 9, it exerts a force on the sensor element 12. In particular, the actuator 5 is arranged to be in direct contact with the sensor element 12 when it is in the actuated configuration.

In this example, the feedback sensor 7 for measuring contact pressure is mounted on the sensor element 12 rather than on the housing.

A coupling member 19 is disposed on the sensor element 12, and is arranged to interface with the user's body in use. In this way, it is possible to maintain a minimum offset between the sensor element 12 and the user's body 2.

The feedback sensor 7 is arranged to measure the pressure of contact between the sensor element 12 and the user's body 2 in use. For example, the feedback sensor 7 is provided on the opposite side on the sensor element 12 to the actuator 5. Together, the feedback sensor 7 and the coupling member 19 may form a surface for interfacing with a user's body. The surface may be substantially planar, or it may be curved to complement the shape of a particular body part for example, an arm.

In use, the feedback sensor 7 measures the pressure of contact between the sensor element 12 and the user's body 2. The feedback sensor 7, for example, is a capacitive sensor, a strain sensor or a piezoelectric sensor. When a change in the pressure of contact is detected, the controller 9 adjusts the actuator 5 wherein movement of the actuator 5 compensates for the detected change in contact pressure. If a decrease in the pressure of contact is detected, the actuator 5 is moved to an actuated position in which the force exerted on the sensor element 12 by the actuator is increased. The force exerted on the sensor element 12 by the actuator 5 pushes the physiological parameter sensor 3 in a direction towards the user's body. If an increase in the pressure of contact is detected, the position of the actuator 5 may be adjusted such that a reduced force is exerted on the sensor element 12. Accordingly, the contact pressure between the physiological parameter sensor 3 and the user's body 2 is reduced.

The actuator 5 is shown in an actuated configuration, wherein the actuator 5 is in contact with the sensor element 12. The actuator is arranged such that when the actuator 5 is in a state of maximum actuation, a maximum actuation force is applied to the sensor element 12. The actuator 5 may be arranged such that when it is in a non-actuated state (very little or no voltage is applied to the actuator) the actuator 5 does not contact the sensor element 12. Alternatively, the actuator 5 may contact the sensor element 12 in both the actuated and the non-actuated state. Alternatively, the actuator may be attached to the sensor element 12 and may be arranged such that in the actuated state the actuator contacts the housing 20 to exerts a force on the housing directly.

Figure 5A:
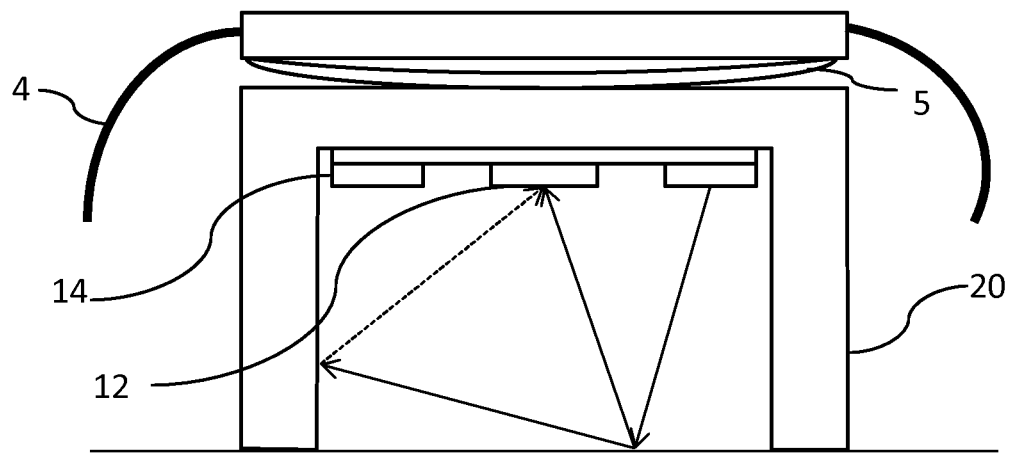
FIGS. 5a to 5c show a wearable device of an apparatus according to another example, in cross section.
Figure 5B:
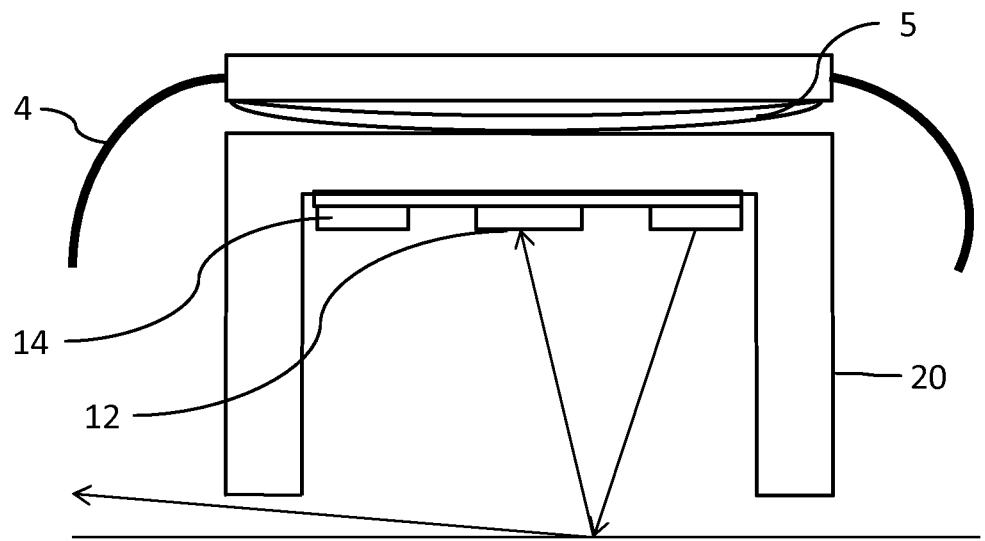
Figure 5C:
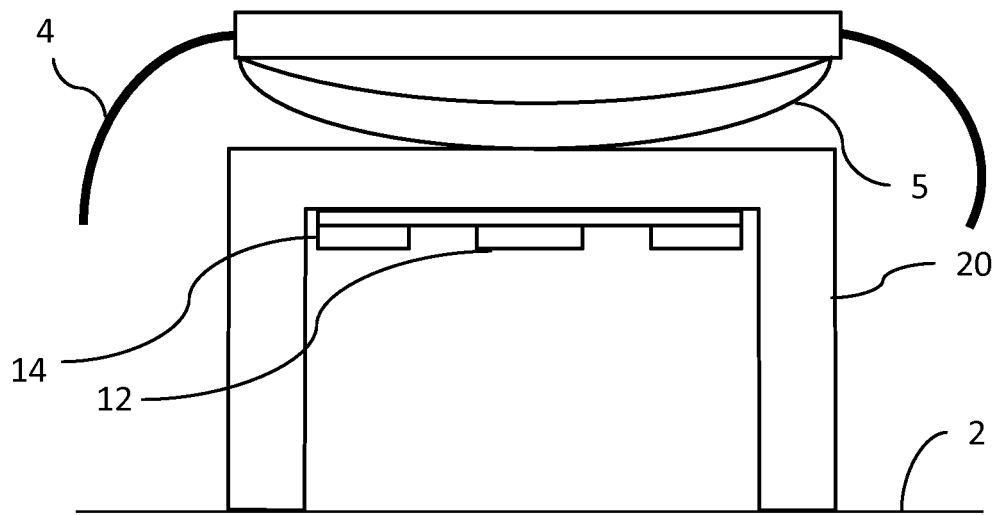

FIGS. 5a-5c show another example, in which the physiological parameter sensor 3 itself implements the feedback sensor 7. In other words, the sensor element 12 of the physiological parameter sensor 3 is inherently capable of sensing relative movement between the physiological parameter sensor 3 and a user's body 2. In an example, the physiological parameter sensor 3 measures a physiological parameter of the subject using light that is reflected or transmitted by a part of the body of the subject. Thus, in these examples, the physiological parameter sensor 3 comprises a light sensor or multiple light sensors 12 for measuring light. The light sensor or each of the multiple light sensors 12 may be sensitive to (i.e. measure) a specific wavelength or a range of wavelengths of light. In some examples the physiological parameter sensor 3 may comprise one or more light sources 14 that output light at one or more specific wavelengths (with the light sensor(s) 12 being sensitive at least to those wavelengths).

The physiological parameter sensor 3 comprises a housing 20 adapted to interface with a user's body 2, with the light source 14 and light sensor 12 disposed within the housing 20. An actuator 5 is provided between the housing 20 and a strap 4 for attaching the physiological parameter sensor to the user's body. The actuator 5 is arranged with respect to the housing 20 such that adjustment of the position of the actuator 5 causes a force to be exerted on the housing 20.

FIG. 5a shows the physiological parameter sensor 3 in contact with a user's body. The light source 14 is arranged inside of the housing 20, and is positioned such that when the physiological parameter sensor is mounted to a user's body, the light source 14 emits light towards the user's body. The light is partly reflected by the user's body 2, and is sensed by the light sensor 12. The reflected light is measured by the light sensor 12, and the measurements are sent to a controller 9 (FIG. 1). The measurements of reflected light made by the light sensor 12 are used to measure a physiological parameter.

FIG. 5b shows the physiological parameter sensor 3 when contact between the physiological parameter sensor 3 and the user's body has been lost. As shown by the arrows, some of the light emitted by the light source 14 is reflected by the user's body and sensed by the light sensor 12. However, some of the light emitted by the light source 14 is lost through a gap between the housing 20 and the user's body. As the housing moves away from the skin, so does light sensor 12, and the signal strength (amplitude or intensity) detected by the light sensor 12 decreases, indicating relative movement between the housing 20 and the user's body. The controller 9 (FIG. 1) may therefore be configured to generate an actuation signal upon detection of a decrease in light intensity. The controller is configured to compare the signal obtained from the light sensor 12 to a threshold value, and to actuate the actuator 5 when the signal received from the light sensor 12 is below the threshold value. Alternatively, the controller may be configured to actuate the actuator 5 when the signal received from the light sensor 12 is above a threshold value, since if ambient light outside of the housing 20 is high, the sensor 12 may measure an increased light level when the housing 20 loses contact with the user's body. In this case, the apparatus 1 may further include an external light sensor (not shown) for measuring the ambient light level and configured to communicate these measurements to the controller. Alternatively, the light source 14 may be interrupted for a short period, allowing the light sensor 12 to uniquely sense ambient light entering the housing.

FIG. 5c shows the physiological parameter sensor 3, after contact between the physiological parameter sensor 3 and the user's body has been re-established. The actuator 5 is in an actuated state, and exerts a force on the housing 20. The force exerted by the actuator 5 on the housing 20 causes the physiological parameter sensor 3 to be pushed towards the user's body. In this way, contact between the housing 20 of the physiological parameter sensor 3 and the subject is re-established.

As the change in light level measured by the sensor 12 as a function of contact is large compared to the change in light level that is measured in physiological parameter measurements, the feedback signal may be separated from the physiological parameter measurement signal so that the two signals do not interfere, for example using a filter. For instance, if the physiological measurement has a certain frequency, the feedback signal may be filtered out using a band-pass filter.

In an alternative example, instead of using the amplitude or intensity of the signal measured by the light sensor to indicate loss of contact, the controller 9 (FIG. 1) may establish loss of contact when a specific wavelength of light is detected by the light sensor 12. For example, if the light source 14 comprises an LED, the controller may establish that contact has been lost if the light sensor 12 senses light having a wavelength different to the wavelength of the LEDs of the light source 14.

In some examples, the controller is configured to apply a first signal to the actuator 5 and a second signal to the light sensor 12 while the physiological parameter sensor 3 is being used. The controller monitors the first and second signal and compares the signals to determine whether contact between the physiological parameter sensor and the user's body has been compromised. The controller may be configured to send the first and second signal to the actuator 5 and the physiological parameter sensor 3 respectively throughout the entire period that the physiological parameter sensor 3 is being used. The first signal and the second signal are AC signals and have substantially the same frequency. In use, when contact between the physiological parameter sensor and the user's body is compromised, light from the light source 14 leaks through the gap between the housing 20 and the user's body. Consequently, the second signal will be modified. As the wearable device begins to become loose, only a small gap will form between the physiological parameter sensor 3 and the user's body and therefore only a small amount of light can leak out of the housing 20. This small leak of light will show up as a ripple in the AC signal. By comparing the first signal to the second signal, it is possible to precisely determine the point at which the physiological parameter sensor 3 first started to lose contact with the user's body. The controller 9 may be configured to calculate the magnitude of the displacement of the physiological parameter sensor 3 with respect to the user's body, and to generate an actuation signal for driving the actuator 5 based on the calculated displacement.

In another example, the physiological parameter sensor is for carrying out ECG measurements and comprises an ECG sensor. The ECG sensor is an electrode which is arranged to be disposed on the subject's body in use. The resistance of the electrode varies with the contact pressure between the subject's body and the electrode. Therefore, the resistance of the ECG sensor may be measured, and the controller may adjust the actuator 5 according to the resistance measurements. For example, the controller may be configured to adjust the actuator if the measured resistance of the ECG electrode is over a threshold value.

In another example, the physiological parameter sensor is for carrying out ultrasound measurements and comprises an ultrasound transducer. A parameter, such as insertion loss, may be measured by the physiological parameter sensor to indicate movement of the physiological parameter sensor relative to the subject. The controller is configured to adjust the position of the actuator 5 according to the measurement of this parameter. For example, the controller may be configured to adjust the actuator 5 if the measured insertion loss is over a threshold value.

Figure 6:
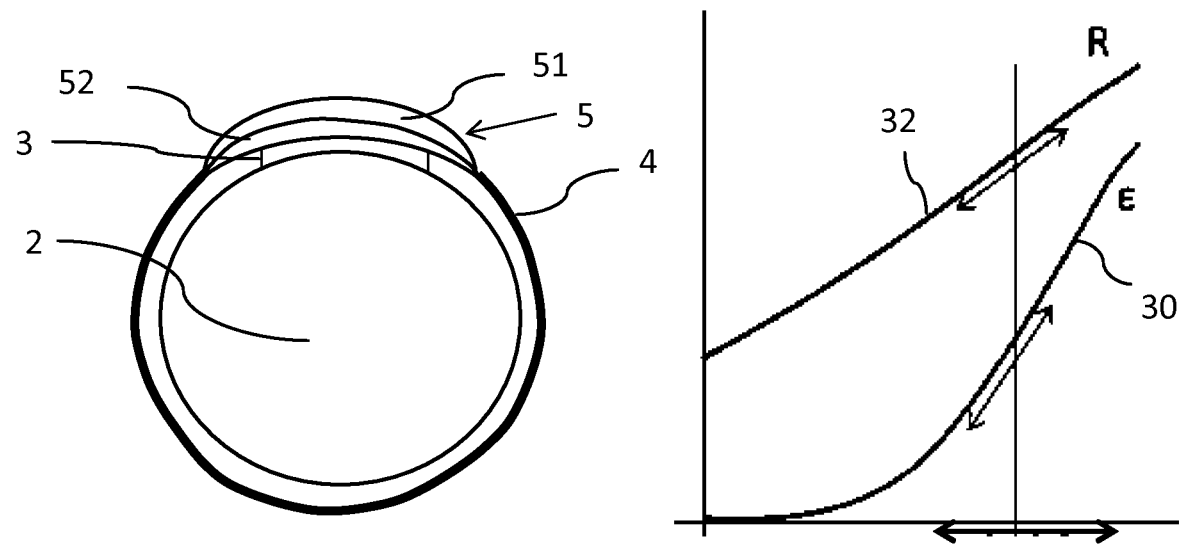
FIG. 6 shows a wearable device of an apparatus according to another example, in cross section.

FIG. 6 shows an example in which the actuator 5 comprises the feedback sensor. It shows a sensor around the wrist of a subject. In other words, the actuator 5 is itself capable of sensing a change in external conditions and is arranged with respect to the physiological parameter sensor 3 in such a way that it is capable of sensing movement of the physiological parameter sensor 3 relative to the user's body 2.

The actuator 5 is attached to the physiological parameter sensor 3 which is arranged to contact a user's body 2 in use. The actuator 5 comprises a first portion and a second portion disposed on the first portion. The first portion 51 is of electroactive polymer material and the second portion is a stretchable strain sensitive electrode 52. The resistivity of the strain sensitive electrode varies with strain; a change in the resistivity of the electrode indicates that the strain in the electrode has changed.

FIG. 6 shows a curve 30 for the measured voltage (x-axis) as a function of the applied strain (y-axis) for the strain sensitive electrode 52 as well as a curve 32 showing the actuation displacement (y-axis) as a function of applied voltage (x-axis).

The actuator 5 is arranged with respect to the physiological parameter sensor 3 such that movement of the physiological parameter sensor 3 relative to the subject's body 2 exerts a force on the actuator 5, and accordingly a strain on the second portion 52 of the actuator. For example, the second portion 52 of the actuator may be disposed between the physiological parameter sensor and the first portion of the actuator 5.

In use, the device is mounted to the user's body, the EAP having a pre-strain and initial voltage below the maximum voltage when the user is static. The resistivity of the electrode is monitored and any change in resistivity can be compensated for by changing the voltage of the EAP actuator to increase or decrease the strain in the EAP portion and to compensate for small positional changes so that the physiological parameter sensor 3 stays in contact with the body 2.

Therefore, by measuring the resistivity of the electrode it is possible to determine whether the physiological parameter sensor 3 has moved relative to the subject's body 2.

The change in resistivity in response to strain is due to the piezoresitivity of the electrode material. The electrode material can be manufactured or selected on the basis of the amount by which the resistivity of the electrode changes in response to a change in strain.

The geometry of the electrode may also be selected in order to optimise the sensitivity of the electrode to changes in strain. An electrode geometry that is particularly sensitive to strain is a meandered electrode (strain gauge). However, if a meandered electrode is used, the distance between the meander tracks of the electrode should be smaller than the thickness of the electroactive polymer portion, in order that the electric field is sufficiently uniform to avoid a loss in the actuator properties of the electroactive polymer portion.

Figure 7:
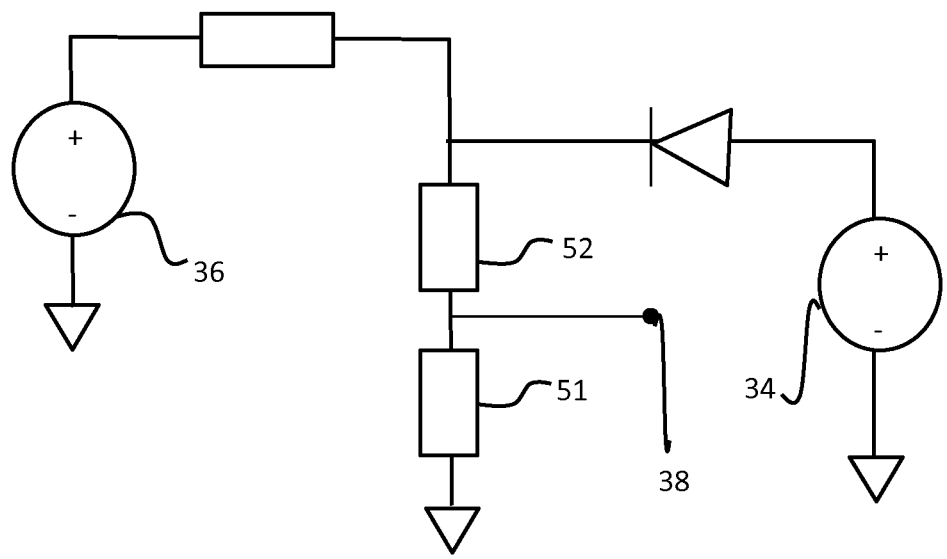
FIG. 7 shows a drive circuit and waveforms.
Figure 7:
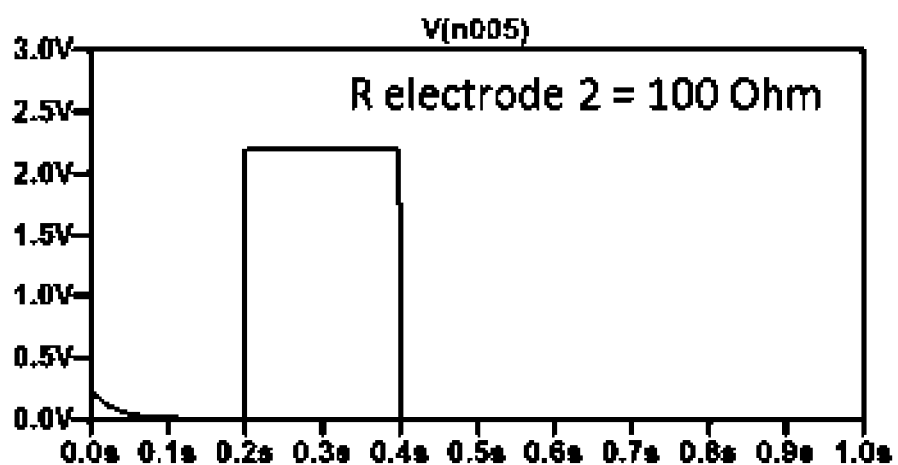
Figure 7:
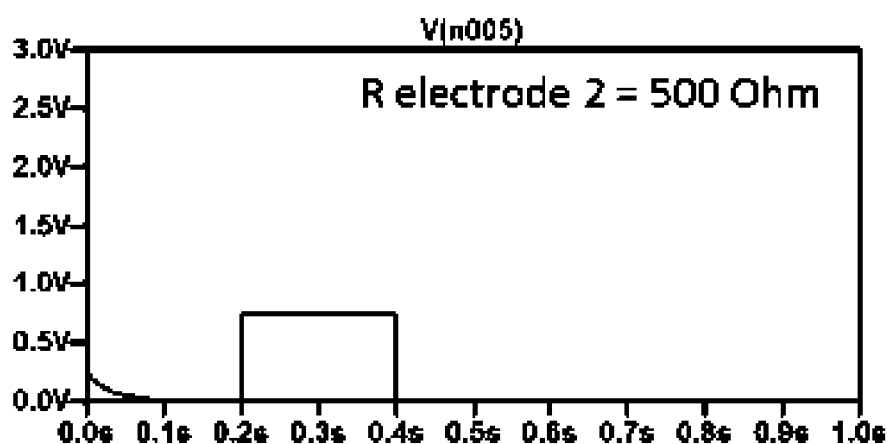

The voltage required to read the strain sensitive electrode is usually lower than the voltage applied to the electro-active portion; therefore strain monitoring is decoupled from the actuator signal. FIG. 7 shows a circuit for decoupling the strain monitoring of the electrode 52 from the actuator signal applied to the EAP actuator layer 51. The circuit has a monitoring voltage source 34 which applies a voltage to the two layers 52, 51 which are electrically in series. A source voltage 36 provides the EAP drive voltage. The readout is at terminal 38 between the two layers 52, 51.

The resistivity of the electrode is measured using a monitoring voltage. A change in the resistivity of the electrode (and therefore a change in the resistance of the electrode) causes a corresponding change in the voltage measured across the electrode. As shown in the example of FIG. 7, an increase in the resistance of the electrode 52 from 100 Ohms (top plot) to 500 Ohms (bottom plot) has a corresponding voltage drop of 2.2 V to 0.7 V. The monitoring voltage is a low voltage, pulsed signal which is applied to the electrode using the controller.

To avoid interference of the monitoring voltage with the actuation voltage (Vsource) the apparatus is configured to apply to monitoring voltage to the electrode even when the maximum actuation voltage is applied to the first portion 51, and the electroactive polymer portion is fully charged. This enables strain to be monitored at full actuation, as well as at other actuation levels.

By providing actuators 5 comprising electroactive polymer material, a high level of contact control is achievable, as the electroactive polymer actuators are thin. Another advantage of these actuators is that they operate using a low power. However, in some applications the maximum actuation of the electroactive polymer actuator alone may not exert a force that is sufficient to correct for a detected change in the relative position of the physiological parameter sensor and the user's body. In general, skin and tissue are relatively flexible and therefore the force required to maintain close contact pressure between a user's body and the wearable part of the apparatus may be high.

Figure 8:
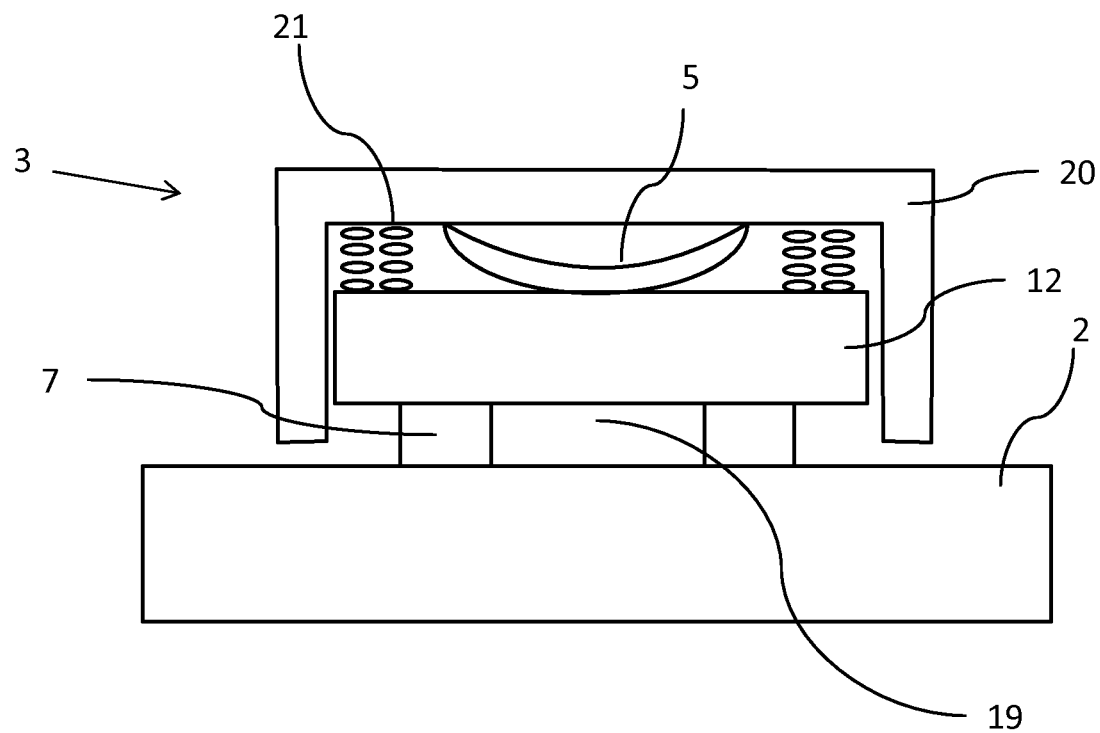
FIG. 8 shows a wearable device of an apparatus according to another example.

FIG. 8 shows a physiological parameter sensor 3 comprising a housing 20, a sensor element 12 disposed within the housing, a coupling member 19 under the sensor element and arranged to interface with a user's body 2 in use, and feedback sensors 7 arranged on either side of the coupling member 19. The device further comprises a biasing member 21 arranged to exert a force on the physiological parameter sensor. The biasing member 21 is a spring, and is positioned within the housing 20 between the roof of the housing and the sensor element 12. The biasing member 21 and actuator 5 are arranged to exert a force on the physiological parameter sensor 3 in the same direction. The biasing member is selected and arranged to exert a force exerted on the housing 20 that is, in combination with the force exerted by the actuator 5, sufficient to establish a desired contact pressure with the user's body. The maximum force exerted by the biasing member 21 and the actuator 5 in combination is greater than the force required to establish the required contact pressure between the subject and the physiological parameter sensor 3 when the user is static. The minimum force exerted by the biasing member 21 and the actuator 5 is sufficient to establish the required contact pressure between the subject and the physiological parameter sensor 3 when the user is static.

FIG. 8 shows the actuator 5 in an actuated state, in which it exerts a maximum force on the physiological parameter sensor, in the same direction as the biasing member 21. By changing the position of the actuator 5, the force exerted on the physiological parameter sensor 3 by the biasing member and the actuator 5 is changed.

In this way, the range of forces which can be applied by the EAP actuator is made to match the required variation in force required, but without the full force needing to be exerted by the actuator.

Figure 9:
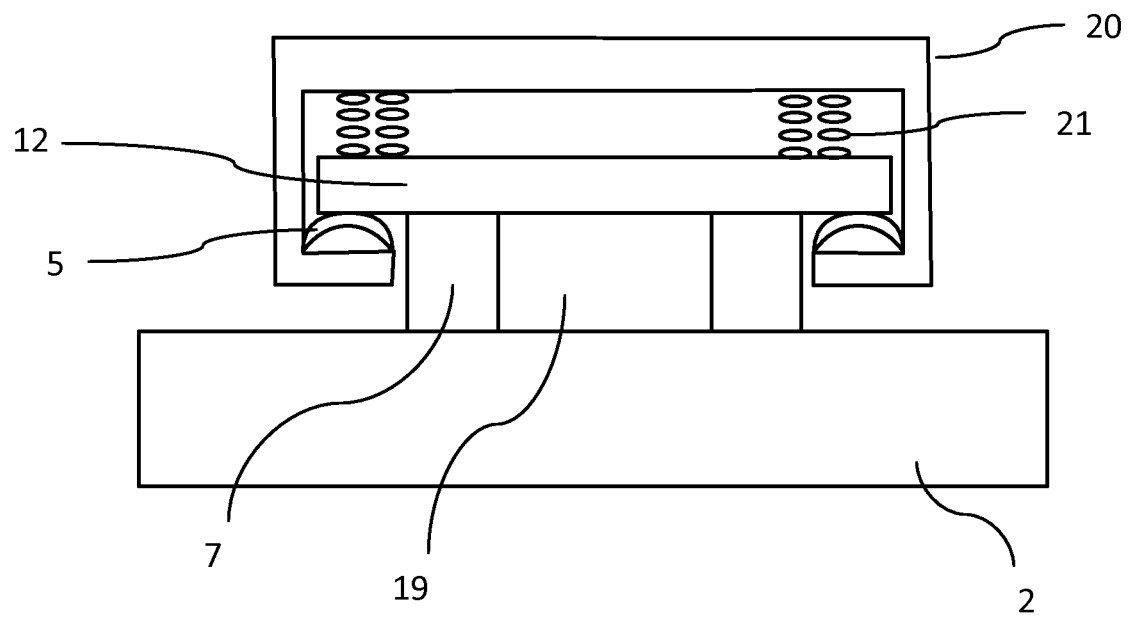
FIG. 9 shows a wearable device of an apparatus according to another example.

FIG. 9 shows a device similar to that of FIG. 8, the device comprising a housing 20, a sensor element 12 disposed within the housing. However, in FIG. 9 the biasing members 21 are arranged to exert a force on the physiological parameter sensor 3 in an opposite direction to the actuator 5. The biasing members 21 exert a force on the physiological parameter sensor 3 that is greater than the force required to establish the required contact pressure between the subject 2 and the physiological parameter sensor 3 when the user is static. The combined force exerted by the actuator 5 at maximum actuation and the biasing member is sufficient to establish the required contact pressure between the subject and the physiological parameter sensor 3 when the user is static.

In the arrangement of FIG. 9, there is an actuator 5 and a feedback sensor 7 on either side of the coupling member 19. In this way, it is possible to provide directional control which enables a user to provide even contact pressure of the interface of the physiological parameter sensor 3 with the user. Thus, by providing an array of at least two sensors and actuators, tilt control becomes possible.

FIGS. 10a and 10b show an arrangement in which the actuator 5 is positioned within the housing 20 of the physiological parameter sensor 3 in such a way that when an actuation signal is sent to the actuator 5, causing it to change shape from a substantially flat configuration to a bowed configuration, a partial local vacuum (i.e. pressure reduction) is formed inside the housing 20 of the physiological parameter sensor, between housing 20 and the actuator 5. This arrangement is suitable for a physiological parameter sensor 3 having a separate feedback sensor 7 (FIG. 1) or an integrated feedback sensor (i.e. the physiological parameter sensor also functions as the feedback sensor).

The wearable device is mounted to a body part of the user, establishing a desired contact pressure or distance of separation between the user's body part and the device. Subsequently, if the feedback sensor detects movement of the wearable device relative to the user's body part, the controller 9 (FIG. 1) sends a signal to actuator 5 causing it to move to an actuated position. FIG. 10a shows the device when contact with the subject 2 has been lost. The actuator 5 has not yet been actuated.

The controller may be configured to cause the actuator to move to the maximum actuated position if any change is detected. Alternatively, the controller may be configured to cause the actuator to a position between the non-actuated position and the maximum actuated position, based on the measurements of the feedback sensor. FIG. 10b shows the device with the actuator in an actuated configuration. This movement of the actuator causes a partial vacuum to form within the housing of the device. In this way, contact between the device and the user's body part 2 is re-established or improved. In an example, multiple actuators 5 are positioned as described above and the controller 9 is configured to actuate the multiple actuators 5 simultaneously.

In some examples, the apparatus comprises a plurality of feedback sensors. The feedback sensors may be provided along the portion of the housing for interfacing with the subject in use, with the portions of the housing intervening between consecutive feedback sensors. Alternatively, the feedback sensors may be provided continuously along the housing.

In some examples, the contact pressure/relative position of the physiological parameter sensor and the user may be continuously adjusted by the actuator in response to a change in contact pressure/relative position measured by the feedback sensor.

The apparatus may include a plurality of actuators which are controlled by the controller to adjust the position of the physiological parameter sensor. The actuators may be controlled to act together, simultaneously or separately.

The actuators may be disposed to exert a force on the housing of the physiological parameter sensor. Alternatively, the actuators may be disposed to exert a force on the sensor element or any other part of the physiological parameter sensor.

The apparatus may comprise a plurality of feedback sensors. Each feedback sensor may have a corresponding actuator or group of actuators which are controller by the controller to adjust the position of the physiological parameter sensor according to the measurement of the corresponding feedback sensor.

The physiological parameter sensor may be provided with a belt, adhesive patch, a watch or as an item of clothing, head or chest band.

The biasing member may be any type of spring, and is preferably a laminated spring, a leaf spring or a plate spring.

Materials suitable for the EAP layer are known. Electro-active polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-tri-fluoroethylene-chlorofluoroethylene (PVDF-TrFE-CFE), Polyvinylidene fluoride-trifluoroethylene-chlorotrifluoro-ethylene) (PVDF-TrFE-CTFE), Polyvinylidene fluoride-hexafluoropropylene (PVDF-HFP), polyurethanes or blends thereof.

The sub-class dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

Ionic devices may be based on ionic polymer-metal composites (IPMCs) or conjugated polymers. An ionic polymer-metal composite (IPMC) is a synthetic composite nanomaterial that displays artificial muscle behaviour under an applied voltage or electric field.

In more detail, IPMCs are composed of an ionic polymer like Nafion or Flemion whose surfaces are chemically plated or physically coated with conductors such as platinum or gold, or carbon-based electrodes. Under an applied voltage, ion migration and redistribution due to the imposed voltage across a strip of IPMCs result in a bending deformation. The polymer is a solvent swollen ion-exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

In all of these examples, additional passive layers may be provided for influencing the electrical and/or mechanical behaviour of the EAP layer in response to an applied electric field.

The EAP layer of each unit may be sandwiched between electrodes. The electrodes may be stretchable so that they follow the deformation of the EAP material layer. Materials suitable for the electrodes are also known, and may for example be selected from the group consisting of thin metal films, such as gold, copper, or aluminium or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminium coating.

Other variations to the disclosed examples can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A wearable sensor apparatus, comprising:
 a sensor element that measures a physiological parameter of a subject;
 an actuator comprising an electro-active polymer material portion that adjusts the position of the sensor element relative to a skin surface of the subject;
 a feedback sensor that measures movement of the sensor element and/or the subject; and
 a controller circuit that processes a signal of the feedback sensor and controls the actuator to adjust the position of the sensor element based on the signal of the feedback sensor,
 wherein the actuator is arranged to adjust the position of the sensor element relative to the subject by exerting a force on the sensor element;
 wherein the sensor element is initially situated at a desired distance from the skin surface of the subject;

wherein the desired distance provides a separation between the sensor element and the skin surface of the subject;

wherein the feedback sensor is configured to measure a change in a distance between the sensor element and the skin surface of the subject relative to the desired distance; and wherein the controller circuit controls the actuator to counteract the change, thereby maintaining the desired distance between the sensor element and the subject.

2. The apparatus of claim 1, wherein the feedback sensor is configured to measure a change in a contact force between the sensor element and the subject.

3. The apparatus of claim 2 further comprising a coupling member disposed on the sensor element and arranged between the sensor element and the subject in use.

4. The apparatus of claim 1, wherein the sensor apparatus comprises: a housing, the housing having walls that define an internal volume; wherein the sensor element is disposed inside the internal volume of the housing, and wherein the feedback sensor is configured to measure movement of the housing relative to the subject.

5. The apparatus of claim 1, wherein the sensor element comprises the feedback sensor, and wherein the controller circuit is configured to process a signal from the sensor element and to adjust the position of the sensor element based on the signal of the sensor element.

6. The apparatus of claim 5, wherein the sensor apparatus comprises:
a housing having walls that define an internal volume;
a light source disposed in the internal volume of the housing; and
an internal light sensor disposed inside the internal volume of the housing,
wherein the controller circuit is configured to process a signal of the internal light sensor and to adjust the position of the actuator based on the signal of the internal light sensor.

7. The apparatus of claim 6 further comprising an exterior light sensor
wherein the exterior light sensor provides signals corresponding to measures of ambient light,
wherein the controller circuit adjusts the position of the actuator based the signals of the exterior light sensor and the internal light sensor.

8. The apparatus of claim 6, further comprising:
a signal generator adapted to:
generate a first electrical alternating signal, for use in sensing, having a first frequency;
generate a second electrical alternating signal, for use in actuation, having a second frequency wherein the second frequency is substantially the same as the first frequency; and
apply the first electrical signal to the sensor element;
apply the second electrical signal to the actuator,
wherein the apparatus further comprises a detector for detecting a difference between the first electrical signal and the second electrical signal.

9. The apparatus of claim 1, wherein the actuator further comprises a strain sensitive electrode portion disposed on an electroactive polymer portion, and the apparatus comprises:
a first power or voltage source arranged to apply a first voltage to the electroactive polymer portion of the actuator; and
a second power or voltage source arranged to apply a second voltage to the strain sensitive electrode portion of the actuator, wherein the controller circuit is arranged to measure a change in resistivity of the strain sensitive electrode and to adjust the position of the sensor element based on the measured change in resistivity.

10. The apparatus of claim 1, wherein the sensor apparatus comprises a housing and the actuator is arranged to exert a force on the housing in response to an actuation signal from the controller circuit.

11. A method comprising:
measuring a physiological parameter of a subject using a sensor element of a sensor apparatus that is worn by the subject;
obtaining a first signal from a feedback sensor of the sensor apparatus;
wherein the first signal is indicative of a placement of the sensor element at a desired distance relative to a skin surface of the subject;
wherein the desired distance provides a separation between the sensor element and the skin surface of the subject;
obtaining a second signal from the feedback sensor;
determining if the sensor element has moved relative to the skin surface of the subject, based on the first and second signals from the feedback sensor;
if the sensor element has moved relative to the skin surface of the subject, adjusting the position of the sensor element based on a difference between first and second signals to maintain the desired distance between the sensor element and the skin surface of the subject,
wherein the actuator exerts a force on the physiological parameter sensor to adjust the position of the sensor element.

12. The method of claim 11, wherein each of the first signal and the second signal comprises a measurement of contact pressure on a surface of the subject.

13. The method of claim 11, further comprising the steps of:
applying a first alternating signal having a first frequency to the actuator;
applying a second alternating signal having a second frequency to the sensor element, wherein the second frequency is the same as the first frequency; and
comparing the first alternating signal and the second alternating signal to determine if the sensor element has moved.

14. The method of claim 11, wherein the feedback sensor is configured to measure a change in contact force between the sensor element and the subject.

15. The method of claim 11, wherein the sensor apparatus comprises a housing having walls that define an internal volume; wherein the sensor element is disposed inside the internal volume of the housing, and wherein the feedback sensor is configured to measure movement of the housing relative to the subject.

16. The method of claim 11, wherein the sensor element comprises the feedback sensor, and wherein the controller circuit is configured to process a signal from the sensor element and to adjust the position of the sensor element based on the signal of the sensor element.

17. The method of claim 16, wherein the sensor apparatus comprises: a housing having walls that define an internal volume; a light source disposed in the internal volume of the housing; and an internal light sensor disposed inside the internal volume of the housing; wherein the method includes processing a signal of the internal light sensor and adjusting the position of the sensor element based on the signal of the internal light sensor.

18. The method of claim 17, wherein the actuator comprises a strain sensitive electrode portion disposed on an electroactive polymer portion, and the method comprises: applying a first voltage to the electroactive polymer portion of the actuator; applying a second voltage to the strain sensitive electrode portion of the actuator; measuring a change in resistivity of the strain sensitive electrode; and adjusting the position of the sensor element based on the measured change in resistivity.

19. The apparatus of claim 1, wherein the feedback sensor comprises a first resistance in series with a second resistance, wherein the first resistance corresponds to a measure of strain on the sensor element, wherein the second resistance corresponds to a measure of resistance of the actuator element, and wherein a node between the first resistance and the second resistance provides the signal of the feedback sensor.

20. The apparatus of claim 19, wherein a continuous source voltage and a pulsed monitoring voltage is applied to the series of the first and second resistances to provide the signal of the feedback sensor.

* * * * *